(12) United States Patent
Wen et al.

(10) Patent No.: US 10,726,951 B2
(45) Date of Patent: Jul. 28, 2020

(54) METHOD AND SYSTEM FOR GENERATING POLYGONS WITHIN A GEOGRAPHIC REGION THAT SATISFY A QUERY

(71) Applicant: Xerox Corporation, Norwalk, CT (US)

(72) Inventors: Xuejin Wen, Fairport, NY (US); Lina Fu, Fairport, NY (US); Jing Zhou, Pittsford, NY (US); Faming Li, Solon, OH (US); Jinhui Yao, Pittsford, NY (US); Michael David Shepherd, Ontario, NY (US); Dennis F. Quebe, Jr., Austin, TX (US)

(73) Assignee: Conduent Business Services, LLC, Dallas, TX (US)

( * ) Notice: Subject to any disclaimer, the term of this patent is extended or adjusted under 35 U.S.C. 154(b) by 542 days.

(21) Appl. No.: 15/154,617

(22) Filed: May 13, 2016

(65) Prior Publication Data
US 2017/0329907 A1  Nov. 16, 2017

(51) Int. Cl.
*G16H 40/20* (2018.01)
*G06F 16/29* (2019.01)

(52) U.S. Cl.
CPC ............ *G16H 40/20* (2018.01); *G06F 16/29* (2019.01)

(58) Field of Classification Search
CPC ..... G06Q 30/0205; G16H 40/20; G06F 16/29
See application file for complete search history.

(56) References Cited

U.S. PATENT DOCUMENTS

| | | | | |
|---|---|---|---|---|
| 7,412,398 B1* | 8/2008 | Bailey | ............. | G06Q 10/06375 705/7.31 |
| 7,746,343 B1* | 6/2010 | Charaniya | ........... | G06F 3/04815 345/428 |
| 8,332,247 B1* | 12/2012 | Bailey | ............. | G06Q 10/06375 705/13 |
| 2008/0278311 A1* | 11/2008 | Grange | .................. | G01C 21/36 340/539.2 |
| 2009/0138445 A1* | 5/2009 | White | .................... | G06Q 30/02 |
| 2012/0313780 A1* | 12/2012 | Stout | .................... | G08B 27/005 340/540 |
| 2013/0132375 A1* | 5/2013 | Jones | .................. | G06F 3/04815 707/722 |

(Continued)

OTHER PUBLICATIONS

John Wennberg and Alan Gittelsohn, Small Area Variations in Health Care Delivery, Science 182 (4117), 1102-1108 (Year: 1973).*

(Continued)

*Primary Examiner* — Andre D Boyce

(57) ABSTRACT

A method and a non-transitory computer readable medium for generating polygons within a geographic region that satisfy a query are disclosed. For example, the method extracts a plurality of nodes, a plurality of service providers and information associated with the plurality of nodes and the plurality of service providers of the geographic region from a geographic data source, creates a node table based on the information that was extracted, receives the query for one or more nodes having a predefined number of service providers within a travel budget, determines the one or more nodes from the node table that satisfy the query, and generates one or more generate polygons around the one or more nodes that satisfy the query within the geographic region.

14 Claims, 7 Drawing Sheets

(56) References Cited

U.S. PATENT DOCUMENTS

| | | | |
|---|---|---|---|
| 2014/0288995 A1* | 9/2014 | Huff | G06Q 10/0635 |
| | | | 705/7.28 |
| 2015/0187107 A1* | 7/2015 | Vander Mey | G06Q 30/00 |
| | | | 345/629 |
| 2017/0098181 A1* | 4/2017 | Herman | G06N 5/022 |
| 2017/0161614 A1* | 6/2017 | Mehta | G06N 5/022 |

OTHER PUBLICATIONS

Mark S. Daskin and Latoya K. Dean, Location of Health Care Facilities, chapter 3 in the Handbook of OR/MS in Health Care: A Handbook of Methods and Applications, F. Sainfort, M. Brandeau and W. Pierskalla, editors, Kluwer, pp. 43-76 (Year: 2004).*

David C. Goodman et al, The Distance to Community Medical Care and the Likelihood of Hospitalization: Is Closer Always Better? American Journal of Public Health, Jul. 1997, vol. 87, No. 7, pp. 1144-1150 (Year: 1997).*

\* cited by examiner

| | LOCATION INFORMATION | NUMBER OF SERVICE PROVIDERS | NUMBER OF PRIMARY CARE PHYSICIANS | NUMBER OF CARDIOLOGIST |
|---|---|---|---|---|
| $210_1$ NODE 1 | | | | |
| $210_2$ NODE 2 | | | | |
| $210_3$ NODE 3 | | | | |
| ⋮ | | | | |
| $210_X$ NODE X | | | | |

FIG. 2

METHOD AND SYSTEM FOR GENERATING POLYGONS WITHIN A GEOGRAPHIC REGION THAT SATISFY A QUERY

The present disclosure relates to generating polygons and more particularly, to a method and a system for generating polygons within a geographic region that satisfy a query.

BACKGROUND

Each state in the United States has its own policy regarding geographic access to healthcare services. For example, the standards may define a measure of access to healthcare services that is required. Different region (e.g., urban counties, rural counties, frontier counties, health districts, and the like) may also have different geographic accessibility requirements.

Current methods to visually display the geographic areas that meet these accessibility requirements can be computationally intensive. In addition, the service coverage maps may not be generated, displayed, or update in real-time and contain outdated information.

SUMMARY

According to aspects illustrated herein, there are provided a method and a non-transitory computer readable medium for generating polygons within a geographic region that satisfy a query. One disclosed feature of the embodiments is a method that extracts a plurality of nodes, a plurality of service providers and information associated with the plurality of nodes and the plurality of service providers of the geographic region from a geographic data source, creates a node table based on the information that was extracted, receives the query for one or more nodes having a predefined number of service providers within a travel budget, determines the one or more nodes from the node table that satisfy the query, and generates one or more polygons around the one or more nodes that satisfy the query within the geographic region.

Another disclosed feature of the embodiments is a non-transitory computer-readable medium having stored thereon a plurality of instructions, the plurality of instructions including instructions, which when executed by a processor, cause the processor to perform operations that extract a plurality of nodes, a plurality of service providers and information associated with the plurality of nodes and the plurality of service providers of the geographic region from a geographic data source, create a node table based on the information that was extracted, receive the query for one or more nodes having a predefined number of service providers within a travel budget, determine the one or more nodes from the node table that satisfy the query, and generate one or more polygons around the one or more nodes that satisfy the query within the geographic region.

Another disclosed feature of the embodiments is an apparatus comprising a processor and a computer-readable medium storing a plurality of instructions which, when executed by the processor, cause the processor to perform operations that extract a plurality of nodes, a plurality of service providers and information associated with the plurality of nodes and the plurality of service providers of the geographic region from a geographic data source, create a node table based on the information that was extracted, receive the query for one or more nodes having a predefined number of service providers within a travel budget, determine the one or more nodes from the node table that satisfy the query, and generate one or more polygons around the one or more nodes that satisfy the query within the geographic region.

BRIEF DESCRIPTION OF THE DRAWINGS

The teaching of the present disclosure can be readily understood by considering the following detailed description in conjunction with the accompanying drawings, in which:

FIG. 2 illustrates an example node table of the present disclosure;

To facilitate understanding, identical reference numerals have been used, where possible, to designate identical elements that are common to the figures.

DETAILED DESCRIPTION

Each state in the United States (U.S.) has its own policy regarding geographic access to healthcare services. For example, for a particular managed care organization (MCO), 90% of its member must have one or more primary care physicians within the state agency pre-defined travel budget (e.g. 30 miles or 30 minutes). This is a measure of access to healthcare services. The geographic area, which is defined by a polygon, within the travel budget from a certain health service provider is considered to be this provider's coverage area. Different regions (e.g., urban counties, rural counties, frontier counties, and the like) may also have different distance requirements.

Current methods to visually display user geographic areas that meet these travel budget requirements can be computationally intensive. In addition, the service coverage maps may not be generated, displayed, or update in real-time and contain outdated information.

Embodiments of the present disclosure provide a novel method for generating polygons within a geographic region that satisfy a query. For example, polygons may be generated in a manner that is computationally more efficient than previously used methods. In addition, the polygons can be updated in real-time. As a result, information associated with the polygons that satisfy the query may contain current information.

In one embodiment, the generated polygons can be used to determine whether the managed care organizations (MCO) adhere to the policy set forth by each state in the U.S. for geographic access to healthcare services. As a result, the generated polygons that satisfy the query can also be used for advanced analysis, such as supply/demand analysis for health systems.

Figure 1:
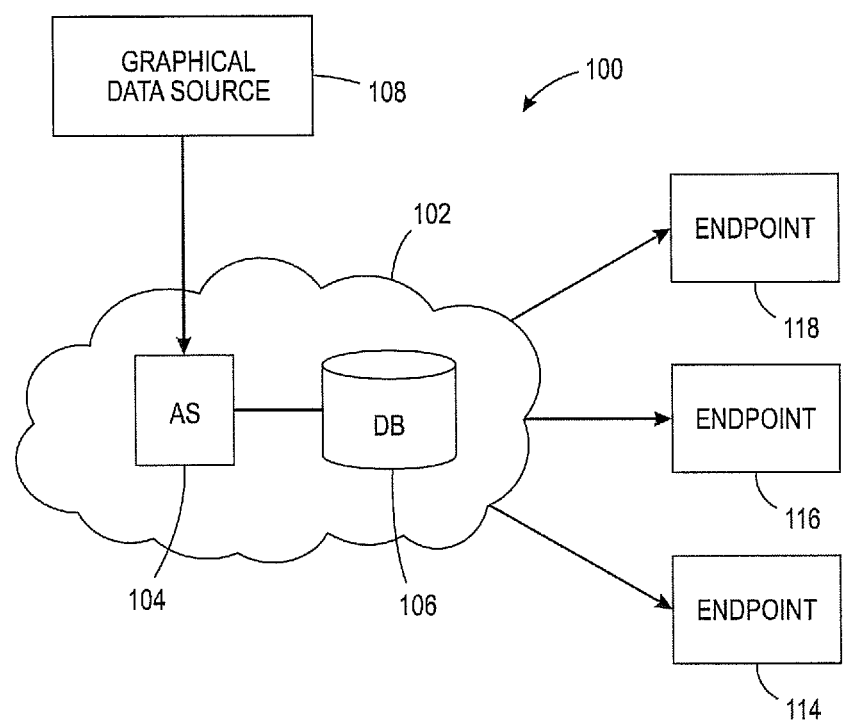
FIG. 1 illustrates a block diagram of an example system of the present disclosure.

FIG. 1 illustrates an example system 100 of the present disclosure. In one embodiment, the system 100 includes a communications network 102. In one embodiment, the communications network 102 may be any type of communications network including, for example, an Internet Protocol (IP) network, a cellular network, a broadband network, and the like. It should be noted that the communications network 102 has been simplified and may contain additional network elements (e.g., gateways, routers, switches, firewalls, access networks, and the like) that are not shown.

In one embodiment, the communications network 102 may include, an application server (AS) 104 and a database (DB) 106. In one embodiment, AS 104 may perform various functions described herein for generating polygons within a geographic region that satisfy a query. In one embodiment, the AS 104 may deployed as a computer illustrated in FIG. 6 and described below and configured to perform the functions described herein.

In one embodiment, the DB 106 may be deployed as a database server that stores various information. For example, the DB 106 may store information that is collected from the geographic data module 108 and the node table. The DB 106 may also store one or more generated polygons, geographic maps annotated with the polygons, and the like.

In one embodiment, the system 100 may include one or more endpoints 114, 116 and 118 that are in communication with the communications network 102. The endpoints 114, 116 and 118 may be any type of endpoint that can transmit data packets over the Internet via a wired or wireless connection. For example, the endpoints 114, 116 and 118 may be a mobile telephone, a smart phone, a desktop computer, a laptop computer, a multi-function device, and the like. In one embodiment, endpoints 114, 116 and 118 may transmit a query to AS 104. Although three endpoints 114, 116 and 118 are illustrated in FIG. 1, it should be noted that there may be any number of endpoints that can transmit packets over the Internet.

In one embodiment, endpoints 114, 116 and 118 may transmit a query to AS 104. In one embodiment, the query may include asking for those nodes that have predefined number of service providers within a parameter, such as a travel budget. In one embodiment, the travel budget may be based on a geographic access standard for access to healthcare for a particular state. For example, some states may require certain geographic areas to have a certain percentage of service providers within a specified distance. For example, New Mexico may require for urban counties, that the travel budget may be within 30 miles, for rural counties, the travel budget may be within 45 miles and for frontier counties, the predefined distance may be within 60 miles. To verify that these requirements are being met, some users may query the AS 104 to see nodes (e.g., residential locations, or members) that have a predefined number of service providers.

In one embodiment, the travel budget may be a driving distance. The driving distance may be measured based upon a distance traveled on an existing street or road. In other words, the driving distance is measured by the length of a street rather than a radial distance outward from a starting point that can traverse undrivable paths as a result of natural and man-made structures, such as lakes, non-developed land, residential and commercial properties, and the like. For example, the distance from a residential patient location to a service provider location may take 15 miles to drive when measured by roads, but may be within five miles when directly measured via the radial distance. In one embodiment, the driving distance may be based on the radial distance.

In another embodiment, the travel budget may be a driving time. For example, the distances may vary based on speed limits, routes, average traffic and the like. Said another way, the travel budget may be based on an amount of time to drive to a service provider rather than a distance to the service provider.

In one embodiment, the AS 104 may answer the query using a node table (e.g., a node table 200 discussed below and illustrated in FIG. 2). The node table may provide an answer that includes the number of nodes that satisfy the query within the parameter. In one embodiment, the AS 104 may draw one or more polygons around the one or more nodes that satisfy the query such that the answer to the query may be output and visually displayed to a user.

In one embodiment, the node table may be generated before the query is received based on information collected from a geographic data source 108. It should be noted that although a single geographic data source 108 is illustrated in FIG. 1, any number of sources may be deployed. The geographic data source 108 may be in communication with the communication network 102 via wired or wireless connection.

In one embodiment, the geographic data source 108 may include data from one or more maps, almanacs, atlases, and the like. The geographic data source 108 may include cross-section of roads, resident location information, service provider location information, and the like. In one embodiment, the location information may be provided in geographic coordinates, such as longitude and latitude values or an address. In one embodiment, based on the service provider location information the AS 104 may identify additional information such as a type of service provider or specialty of the service provider. For example, the type of service provider may include a primary care physician, a pharmacist, a Federally Qualified Health Center, a pediatrician, a cardiologist, an oncologist, and the like.

In one embodiment, the AS 104 may identify nodes from the geographic data source 108. For example, the nodes may include locations that have a residential address. The AS 104 may exclude nodes that are in uninteresting areas such as a body of water, an open field, and the like. The AS 104 may then associate each node with the corresponding location information obtained from the geographic data source 108.

With the information obtained from the geographic data source 108, the AS 104 may generate a node table 200 as illustrated in FIG. 2. In one embodiment, the node table 200 may include a plurality of rows $210_1$ to $210_x$ (herein also referred to individually as a row 210 or collectively as rows 210). In one embodiment, the number of rows 210 may be equal to the number of nodes. In other words, the node table 200 may have one row 210 for each node that was identified by the AS 104 from the geographic data source 108.

In one embodiment, the node table 200 may include a plurality of columns 202, 204, 206 and 208. In one embodiment, the column 202 may include location information for a respective node. In one embodiment, the column 204 may include a number of service providers 204 that are within a travel budget around the respective node. In one embodiment, the travel budget may be based on the requirements for each state as described above. In one embodiment, the columns 206 and 208 may be optional and include information for a particular specialist. For example, the column 206 may include a number of primary care physicians within the travel budget and the column 208 may include a number of cardiologists within the travel budget. It should be noted that additional columns may be added for other specialists such as oncologists, pediatric care providers, and the like.

In one embodiment, the information in the column 204 may be obtained by the AS 104 and updated continuously. In other words, as service providers and residents (e.g., the nodes) are being continuously added and subtracted, the AS 104 may continuously pull the information from the geographic data source 108 and update the values for the column 204. As a result, the answers the query may always provide the most updated results or information. In one embodiment, the node table 200 may be stored in and accessed from the DB 106.

Figure 3:
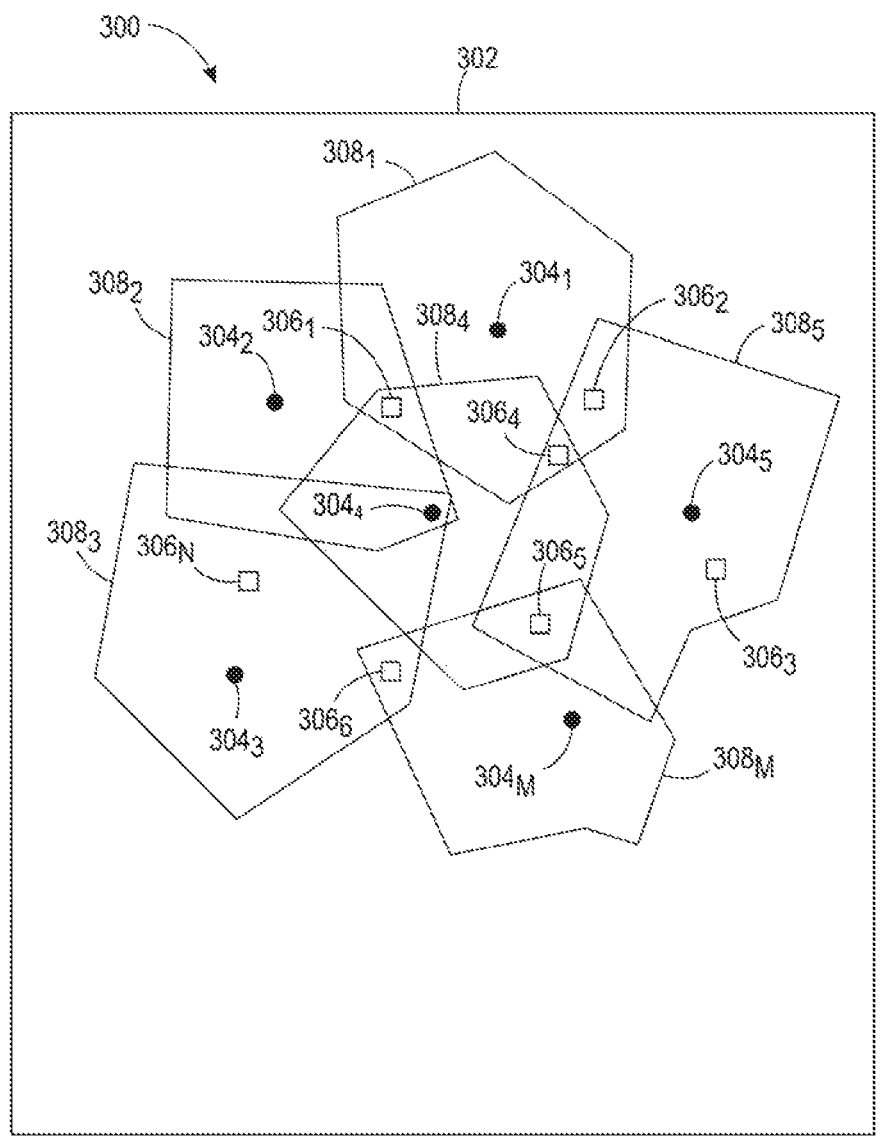
FIG. 3 illustrates an example intermediate step for building the node table of the present disclosure.

In one embodiment, the AS 104 may perform an intermediate step 300 illustrated in FIG. 3 to obtain the information for the column 204. In one embodiment, for a region 302 (e.g., a state, a county, a city, and the like), there may be service providers $304_1$ to $304_m$ (herein also referred to individually as a service provider 304 or collectively a service providers 304) identified from the geographic data source 108. In one embodiment, the region 302 may be a map obtained from the geographic data source 108 that may include cross-roads, sources of water, country boundaries, and the like that may be seen from a map.

In one embodiment, nodes $306_1$ to $306_n$ (herein also referred to individually as a node 306 or collectively as nodes 306) may also be identified from the geographic data source 108, as described above. For each one of the service providers 304, a number of nodes 306 served by each respective service provider 304 within a predetermined travel budget may be determined. Conceptually, the travel budge may be illustrated by a respective polygon $308_1$ to $308_m$ (herein also referred to individually as a polygon 308 or collectively as polygons 308) that could be drawn around each service provider $304_1$ to $304_m$. It should be noted that the polygons 308 are provided as an example to help conceptualize the boundary around each service provider 304 created by the travel budget.

In one embodiment, the shape of the polygons 308 may vary based on the travel budget (e.g., driving distance or driving time). As discussed above, the travel budget may be measured based on the actual roads or variables that can affect driving time and not a straight radius around a location of a service provider 304 that includes impassable or undrivable areas.

The AS 104 may then track a number of service providers 304 that are covered for each node 306. For example, the node $306_1$ may be covered by three service providers (e.g., service providers $304_1$, $304_2$ and $304_4$). The node $306_2$ may be covered by two service providers (e.g., service providers $304_1$ and $304_5$), and so forth. For each node 306, the node table 200 would be updated to include the corresponding number of service providers that cover the respective node in the column 204.

In one embodiment, the table 200 may include multiple columns 204 for a number of service providers within different travel budgets that can be queried. For example, the number of columns may be equivalent to the number of different travel budgets that are associated with the respective geographic access standard. For example, a first column 204 may be for a number of service providers within 30 miles, a second column 204 may be for a number of service providers within 45 miles, a third column 204 may be for a number of service providers within 60 miles, and the like.

In one embodiment, the optional columns 206 and 208 may be updated similarly for a particular specialist. For example, for primary care physicians (PCP) polygons may be drawing around each PCP and the number of nodes covered by each PCP may be entered in the optional column 206.

In one embodiment, the intermediate step 300 may be continuously performed as new service providers 304 or nodes 306 are added or service providers 304 or nodes 306 are removed. In one embodiment, the intermediate step 300 may be performed periodically (e.g., every hour, every day, every week, and the like).

As a result, the node table 200 may be used to answer the query from an endpoint device 114, 116 or 118. For example, the endpoint device 114 may query the AS 104 to ask how many nodes are covered by at least three service providers within a 30 mile radius. In response to the query, the AS 104 may analyze the node table 200 to determine the nodes that satisfy the query. Using the example from FIG. 3 as an example, the polygon 308 may have been drawn based on the 30 mile requirement. The AS 104 may identify three nodes 306 that satisfy the query (e.g., nodes $306_1$, $306_2$ and $306_5$). The AS 104 may then transmit the answer to the query back to the endpoint device 114.

Figure 4:
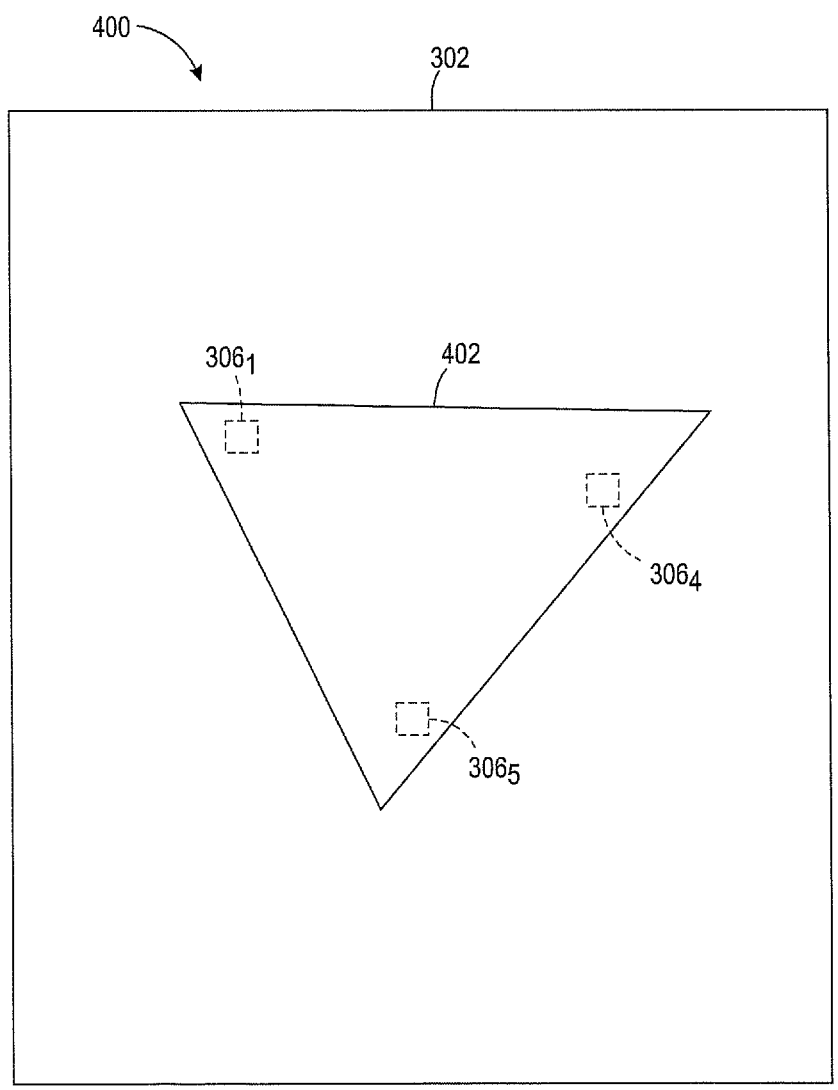
FIG. 4 illustrates an example final display of generated polygons within a geographic region that satisfy a query of the present disclosure.

In one embodiment, the AS 104 may generate one or more polygons based on the answer to the query to allow the endpoint device 114 to visually display the answer to the query. FIG. 4 illustrates one example of a final display 400 that includes a polygon 402. The final display 400 may include the same geographic region 302 that was used to perform the intermediate step 302. For example, the geographic region 302 may be a map that was obtained from the geographic data source 108 and the AS 104 may annotate the map with the polygon 402. In other words, the map may be modified or changed by the AS 104 to include the polygon 402. The polygon 402 may include the region that includes the nodes (e.g., $306_1$, $306_2$ and $306_5$ illustrated in dashed lines) that satisfy the query from the endpoint device 114. In one embodiment, the AS 104 may generate a list of nodes from the node table 200 that satisfy the query. The list may be transmitted to the endpoint 114 via the communication network 102 in addition to the annotated map of the geographic region 302 that includes the polygon 402.

It should be noted that a single polygon 402 is illustrated for ease of explanation. However, a plurality of polygons 402 may be generated and displayed in different areas of the geographic region 302 that satisfy the query.

It should be noted that although embodiments of the present disclosure are described with respect to service providers, the present disclosure may be applied to any application that requires identification of a number of service providers for each node within a travel budget. For example, the present disclosure may be used to verify a number of schools within a geographic region that serve each node, a number of public services within a geographic region that serve each node, and the like.

Figure 5:
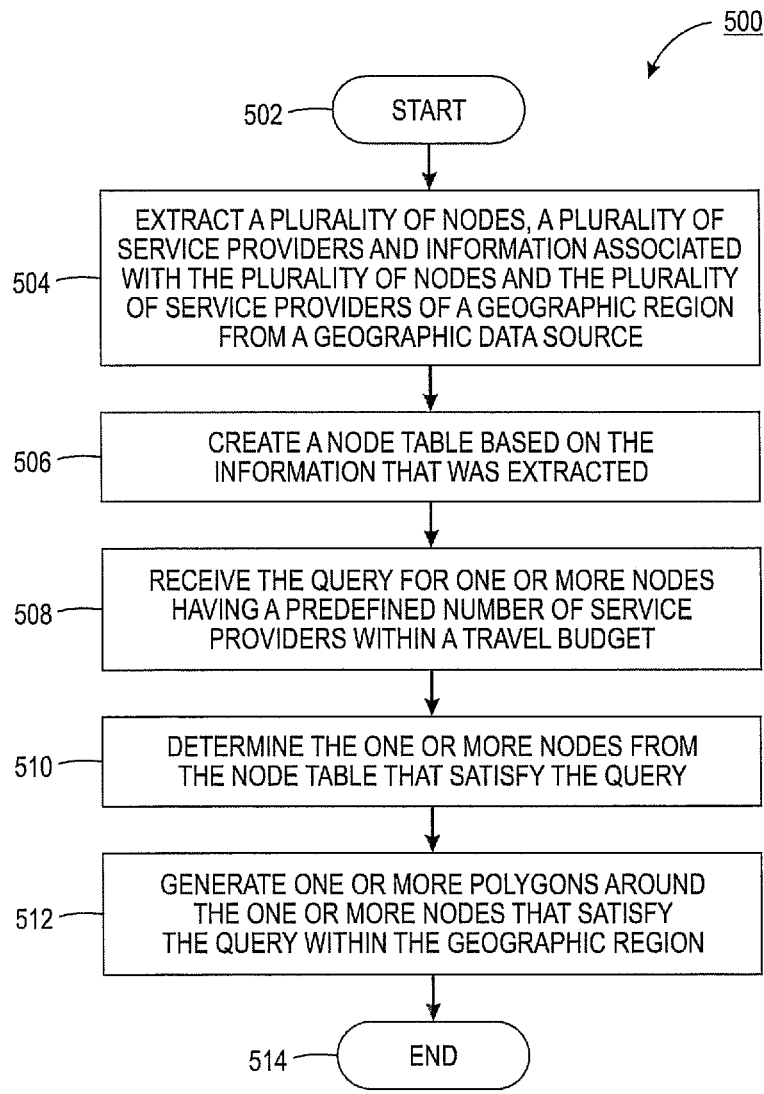
FIG. 5 illustrates a flowchart of an example method for generating polygons within a geographic region that satisfy a query of the present disclosure.
Figure 7:
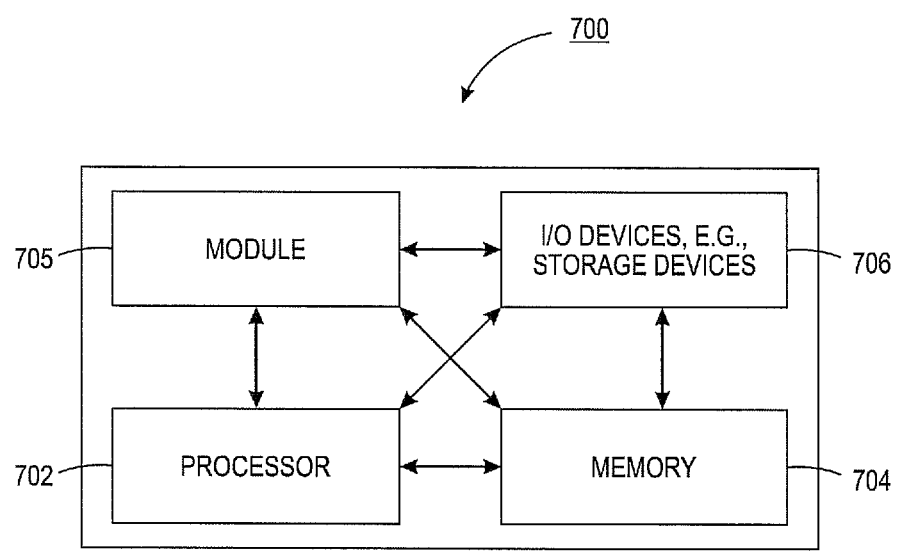
FIG. 7 illustrates a high-level block diagram of a computer suitable for use in performing the functions described herein.

FIG. 5 illustrates a flowchart of an example method for generating polygons within a geographic region that satisfy a query of the present disclosure. In one embodiment, one or more blocks or operations of a method 500 may be performed by the AS 104 or a computer as illustrated in FIG. 7 and discussed below.

At block 502 the method 500 begins. At block 504, the method 500 extracts a plurality of nodes, a plurality of service providers and information associated with the plurality of nodes and the plurality of service providers of a geographic region from a geographic data source. For example, the geographic data source may include data that can be used to identify the nodes and the service providers. In addition, information associated with the service providers such as an address or geographic coordinates may be obtained.

At block 506, the method 500 creates a node table based on the information that was extracted. In one embodiment, the node table may be created that identifies how many service providers serve each identified node within a travel budget. For example, the travel budget may be based on a geographic access standard.

In one embodiment, the information for each column that identifies how many service providers that serve each node may be obtained by performing an intermediate step. For example, a polygon that is defined by the travel budget may be drawn around each service provider. Then for each node, the number of service provider polygons that include the node may be counted. The number of service providers that serve each node may be calculated in this way.

At block 508, the method 500 receives the query for one or more nodes having a predefined number of service providers within the travel budget. In one embodiment, a user may wish to verify if certain nodes and/or service providers are meeting the requirements of the geographic access standards. As a result, the user may send a query via an endpoint to ask how many nodes are serviced by a certain number of service providers within the travel budget. For example, the user may set the predefined number of service providers in the query and the travel budget may be based off of the geographic access standard for a particular region.

At block 510, the method 500 determines the one or more nodes from the node table that satisfies the query. For example, after the query is received, the query may be answered by looking for the nodes in the node table that satisfy the query. In one embodiment, a list of nodes that satisfy the query may be generated.

At block 512, the method 500 generates one or more polygons within the geographic region based on the list of nodes from the node table that satisfies the query. For example, map of the geographic region may be annotated or modified with the one or more polygons that are generated. Each polygon may represent an area that includes the nodes identified from the node table that satisfy the query. The annotated map with the one or more polygons may quickly show a user which regions have a sufficient number of service providers.

In one embodiment, the annotated map with the one or more polygons may be transmitted to a health service provider system that can then send a notification to service providers if they do not meet the requirements of a respective geographic access standard. In other words, the annotated map may be transmitted over a communication network from the AS that generated the annotated map to an endpoint. The annotated map may be further used to cause a health service provider system to take action based upon the annotated map. At block 514 the method 500 ends.

Figure 6:
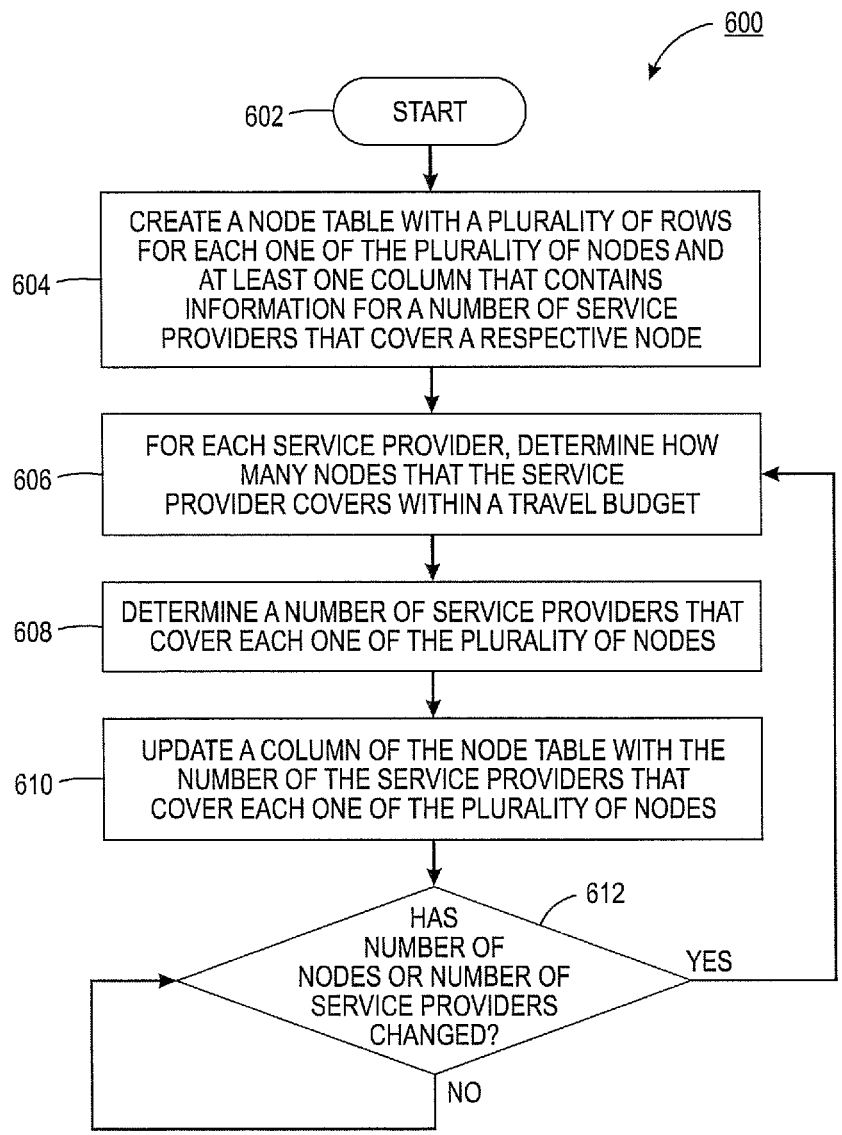
FIG. 6 illustrates a flowchart of an example method for creating a node table.

FIG. 6 illustrates a flowchart for an example method for creating the node table. In one embodiment, one or more blocks or operations of method 600 may be performed by the AS 104 or a computer as illustrated in FIG. 7 and discussed below.

At block 602, the method 600 begins. At block 604, the method 600 creates a node table with a plurality of rows for each one of the plurality of nodes and at least one column that contains information for a number of service providers that cover a respective node. In some examples, the node table may include additional columns for different specialties of service providers. An example of the node table is illustrated in FIG. 2 and described above.

At block 606, the method 600, for each service provider, determines how many nodes that the service provider covers within a travel budget. For example, the travel budget may create a boundary around each service provider that is conceptualized as imaginary polygons illustrated in FIG. 3 and described above.

At block 608, the method 600 determines a number of service providers that cover each one of the plurality of nodes. For example, each non-service provider node may be examined to count how many polygons encompass, or cover, the node. This process may be repeated for each node in the node table. In other words, for each row in the node table that represents a node, the number of service providers that cover the node may be counted and tracked. Non-interesting nodes (e.g., nodes that are associated with a body of water, unoccupied land, and so forth) may be skipped over.

At block 610, the method 600 updates a column of the node table with the number of the service providers that cover each one of the plurality of nodes. For example, each row of the node table may correspond to a node. The number of service providers that cover the node, determined in the bock 608 above, may be updated in a field that corresponds to a respective row and column of the node table. At this point, the initial node table may be completed and ready to be used for queries.

At block 612, the method 600 may determine if the number of nodes or the number service providers has changed. For example, after the node table is initially created and initialized, the number of nodes and service providers can change. If the number of nodes or the number of service providers has not changed, the method 600 may continuously loop back to block 612 until a change is detected.

If the number of nodes or the number of service providers has changed, the method 600 may return to block 606 and the method 600 may be repeated to update the node table. For example, for each service provider, the number of nodes covered by the service provider within the travel budget may be counted again and the number of service providers that cover each node may be updated.

As a result, the embodiments of the present disclosure utilize a building and query process for generating polygons within a geographic region that satisfy a query. As a result, polygons that satisfy the query are generated, updated, and displayed in real-time with current information. As a result, the generated polygons can be used to determine whether the managed care organizations (MCO) adhere to the policy set forth by each U.S. state for geographic access to healthcare services. As a result, the generated polygons that satisfy the query can also be used for advanced analysis, such as supply/demand analysis for health systems.

FIG. 7 depicts a high-level block diagram of a computer that can be transformed to into a machine that is dedicated to perform the functions described herein. As depicted in FIG. 7, the computer 700 comprises one or more hardware processor elements 702 (e.g., a central processing unit (CPU), a microprocessor, or a multi-core processor), a memory 704, e.g., random access memory (RAM) and/or read only memory (ROM), a module 705 for generating polygons within a geographic region that satisfy a query, and various input/output devices 706 (e.g., storage devices, including but not limited to, a tape drive, a floppy drive, a hard disk drive or a compact disk drive, a receiver, a transmitter, a speaker, a display, a speech synthesizer, an output port, an input port and a user input device (such as a keyboard, a keypad, a mouse, a microphone and the like)). Although only one processor element is shown, it should be noted that the computer may employ a plurality of processor elements. Furthermore, although only one computer is shown in the figure, if the method(s) as discussed above is implemented in a distributed or parallel manner for a particular illustrative example, i.e., the steps of the above method(s) or the entire method(s) are implemented across multiple or parallel computers, then the computer of this figure is intended to represent each of those multiple computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 705 for generating polygons within a geographic region that satisfy a query (e.g., a software program comprising computer-executable instructions) can be loaded into memory 704 and executed by hardware processor element 702 to implement the steps, functions or operations as discussed above in connection with the exemplary methods 500 and 600. Furthermore, when a hardware processor executes instructions to perform "operations," this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 705 for generating polygons within a geographic region that satisfy a query (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for generating one or more polygons within a geographic region that satisfy a query, comprising:
    extracting, by a processor, a plurality of nodes, a plurality of service providers and information associated with the plurality of nodes and the plurality of service providers of the geographic region from a geographic data source, wherein each one of the plurality of nodes represents a residential address;
    creating, by the processor, a node table based on the information that was extracted, wherein the node table includes the plurality of nodes and a number of health service providers within different travel budgets for each one of the plurality of nodes;
    receiving, by the processor, the query, wherein the query asks how many nodes are covered by a predefined number of health service providers within a travel budget to satisfy a policy set forth by different states for managed care organizations, wherein the travel budget is based on a geographic access standard for access to healthcare for a particular state that requires a certain percentage of service providers within a specified distance, wherein the specified distance is measured based on driving distance on existing streets and not a radial distance measured from a starting point that traverses undrivable paths;
    determining, by the processor, a number of nodes from the node table that satisfy the query;
    generating, by the processor, a polygon around the number of nodes that satisfy the query within the geographic region; and
    displaying, by the processor, the polygon that includes the number of nodes to visualize an answer to the query that includes the number of nodes.

2. The method of claim 1, wherein the information comprises location information comprising geographic coordinates or an address.

3. The method of claim 1, wherein the predefined number of service providers of the query comprises a number of a particular type of service provider.

4. The method of claim 1, further comprising:
    transmitting, by the processor, the map of the geographic region that is annotated with the one or more polygons to an endpoint device that displays the geographic region that is annotated with the one or more polygons.

5. The method of claim 1, wherein the node table comprises a plurality of rows that represent each one of the plurality of nodes and a plurality of columns that represent location information associated with a respective one of the plurality of nodes and a number of service providers within the travel budget for the respective one of the plurality of nodes.

6. The method of claim 1, wherein the creating the node table comprises:
    determining, by the processor, a number of nodes served by each one of the plurality of service providers within a boundary defined by the travel budget; and
    determining, by the processor, a number of service providers that cover each one of the plurality of nodes.

7. The method of claim 1, further comprising:
    determining, by the processor, the plurality of nodes or the plurality of service providers has changed;
    updating, by the processor, the node table; and
    redrawing, by the processor, the one or more polygons based on the updating.

8. A non-transitory computer-readable medium storing a plurality of instructions, which when executed by a processor, cause the processor to perform operations for generating one or more polygons within a geographic region that satisfy a query, the operations comprising:
    extracting a plurality of nodes, a plurality of service providers and information associated with the plurality of nodes and the plurality of service providers of the geographic region from a geographic data source, wherein each one of the plurality of nodes represents a residential address;

creating a node table based on the information that was extracted, wherein the node table includes the plurality of nodes and a number of health service providers within different travel budgets for each one of the plurality of nodes;

receiving the query, wherein the query asks how many nodes are covered by a predefined number of health service providers within a travel budget to satisfy a policy set forth by different states for managed care organizations, wherein the travel budget is based on a geographic access standard for access to healthcare for a particular state that requires a certain percentage of service providers within a specified distance, wherein the specified distance is measured based on driving distance on existing streets and not a radial distance measured from a starting point that traverses undrivable paths;

determining the a number of nodes from the node table that satisfy the query;

generating a polygon around the number of nodes that satisfy the query within the geographic region; and displaying the polygon that includes the number of nodes to visualize an answer to the query that includes the number of nodes.

9. The non-transitory computer-readable medium of claim 8, wherein the information comprises location information comprising geographic coordinates or an address.

10. The non-transitory computer-readable medium of claim 8, further comprising:
transmitting the map of the geographic region that is annotated with the one or more polygons to an endpoint device that displays the geographic region that is annotated with the one or more polygons.

11. The non-transitory computer-readable medium of claim 8, wherein the node table comprises a plurality of rows that represent each one of the plurality of nodes and a plurality of columns that represent location information associated with a respective one of the plurality of nodes and a number of service providers within the travel budget for the respective one of the plurality of nodes.

12. The non-transitory computer-readable medium of claim 8, wherein creating, by the processor, the node table comprises:
determining a number of nodes served by each one of the plurality of service providers within a boundary defined by the travel budget; and
determining a number of service providers that cover each one of the plurality of nodes.

13. The non-transitory computer-readable medium of claim 8, further comprising:
determining the plurality of nodes or the plurality of service providers has changed;
updating the node table; and
redrawing the one or more polygons based on the updating.

14. A method for generating one or more polygons within a geographic region that satisfy a query, comprising:
extracting, by a processor, a plurality of nodes, a plurality of service providers and information associated with the plurality of nodes and the plurality of service providers of the geographic region from a geographic data source, wherein each one of the plurality of nodes represents a residential address;

determining, by the processor, a number of nodes of the plurality of nodes served by each one of the plurality of service providers within a boundary defined by different travel budgets;

determining, by the processor, a number of service providers that cover each one of the plurality of nodes for the different travel budgets;

creating, by the processor, a node table based, wherein the node table comprises a row for the each one of the plurality of nodes, a first column comprising location information for the each one of the plurality of nodes and a second column comprising the number of service providers that cover the each one of the plurality of nodes, wherein the node table is continuously updated;

receiving, by the processor, the query, wherein the query asks how many nodes are covered by a predefined number of health service providers within the travel budget to satisfy a policy set forth by different states for managed care organizations, wherein the travel budget is based on a geographic access standard for access to healthcare for a particular state that requires a certain percentage of service providers within a specified distance, wherein the specified distance is measured based on driving distance on existing streets and not a radial distance measured from a starting point that traverses undrivable paths;

determining, by the processor, a number of nodes from the node table that satisfy the query;

generating, by the processor, a polygon around the number of nodes that satisfy the query within the geographic region; and displaying, by the processor, the polygon that includes the number of nodes to visualize an answer to the query that includes the number of nodes.

* * * * *